United States Patent [19]

Grey

[11] 4,451,672

[45] May 29, 1984

[54] PREPARATION OF KETONES FROM 1,2-EPOXIDES

[75] Inventor: Roger A. Grey, West Chester, Pa.

[73] Assignee: Atlantic Richfield Company, Los Angeles, Calif.

[21] Appl. No.: 462,253

[22] Filed: Jan. 31, 1983

[51] Int. Cl.$^3$ .............................................. C07C 45/58
[52] U.S. Cl. .................................................... 568/384
[58] Field of Search ................................ 568/384, 386

[56] References Cited

U.S. PATENT DOCUMENTS

| 2,799,708 | 7/1957 | Oakley et al. | 568/384 |
| 3,151,167 | 9/1964 | Eisenmann et al. | 568/384 |
| 3,542,883 | 11/1970 | Nenitescu et al. | 568/384 |

*Primary Examiner*—James H. Reamer
*Attorney, Agent, or Firm*—Craig E. Larson

[57] ABSTRACT

Methyl ethyl ketone is produced in quantitative yields by isomerizing 1,2-butylene oxide or isomeric mixtures of n-butylene oxides in the presence of a tertiary butyl alcohol solution of dicobalt octacarbonyl.

2 Claims, No Drawings

PREPARATION OF KETONES FROM 1,2-EPOXIDES

BACKGROUND OF THE INVENTION

1. Field of the Invention

This invention relates to the preparation of ketones by the catalytic isomerization or molecular rearrangement of epoxides. This invention particularly relates to the isomerization of 1,2-epoxides in alcohol solutions of dicobalt octacarbonyls.

2. Description of the Prior Art

As a general rule, the predominant isomerization product of 1,2-epoxides using soluble Lewis acids or heterogeneous catalysts is the corresponding aldehyde. By contrast, the predominant isomerization product of internal epoxides under similar isomerization conditions is the corresponding ketone.

Although 1,2-epoxide isomerization generally favors molecular rearrangement of oxygen towards the alpha carbon atom of the epoxide, ketones have been prepared by the isomerization of 1,2-epoxides in the presence of alkanol solutions of dinuclear carbonyls. Eisenmann, J. L., *J. Org. Chem.*, 27, 2706 (1962) and U.S. Pat. No. 3,151,167. According to the '167 patent, suitable alkanols for this reaction are primary and secondary, mono- and dihydroxy lower alkanes, especially methanol, isopropanol and primary and secondary butanol. Methanol was particularly preferred. Suitable dinuclear carbonyls (disclosed in the '167 patent) are dicobalt octacarbonyl, dirhodium octacarbonyl and diiridium octacarbonyl. The latter compounds—dirhodium and diiridium octacarbonyls—have subsequently been shown to be nonexistent. Bor and Noack, *J. Organometal Chem.*, 64, 367(1974).

SUMMARY OF THE INVENTION

It has now been found that nearly guantitative yields of methyl ethyl ketone are obtained when 1,2-butylene oxide or isomeric mixtures of n-butylene oxides are isomerized with a tertiary butyl alcohol solution of dicobalt octacarbonyl ($[Co(CO)_4]_2$).

DETAILED DESCRIPTION OF THE INVENTION

As used herein, the term "isomeric mixture of n-butylene oxide" is intended to include mixtures of 1,2-butylene oxide with 2,3-butylene oxide (in either or both of its isomeric forms).

According to the method of this invention, dicobalt octacarbonyl is added to tertiary butyl alcohol and the mixture is stirred for a period of time to form a solution of the catalyst. Then 1,2-butylene oxide or an isomeric mixture of n-butylene oxide is added to the solution and nearly quantitative yields of methyl ethyl ketone are obtained. The ketone may be separated from the reaction mixture by conventional distillation and filtration procedures.

Preferably, the temperature of the reaction mixture is maintained near ambient temperatures, although temperatures within the range of about 0° to 100° C. may be employed. The proportions of the reactants do not appear to be critical and may vary over a wide range.

Preferably, the reaction is carried out in an inert atmosphere such as nitrogen, argon, helium, etc.

The following examples demonstrate the process of this invention and the unexpected results obtained thereby.

EXAMPLE I

In a 50 ml. three-necked flask equipped with thermometer, reflux condenser, addition funnel, and magnetic stirrer, 600 mg. of dicobalt octacarbonyl was added to 6 ml. of tertiary butyl alcohol under an argon atmosphere and stirred for 1 hour. No gas evolution was observed. Then, 6 ml. of 1,2-butylene oxide was added via the addition funnel over a 10 minute period. No exotherm or color change was observed. Stirring continued at 25°–30° C. for 6 hours, at which time the mixture was heated to 50° C. and maintained at that temperature for ½ hour. The reaction mixture was analyzed by gas chromatography and the product was found to contain essentially only methyl ethyl ketone (98 wt. %+). A small amount of hydroxy ethers (less than 1%) was also present.

EXAMPLE II

Using the same apparatus described in Example 1, 600 mg. of dicobalt octacarbonyl was added to 6 ml. of tertiary butyl alcohol under an argon atmosphere and stirred for 1 hour at 30° C. No exotherm or gas evolution was observed. Then 6 ml of 1,2-butylene oxide; cis-2,3-butylene oxide; and trans-2,3-butylene oxide was added via the addition funnel over a 2 minute period. The weight ratio of the butylene oxide feed components was 81 1,2-butylene oxide:4.5 cis-2,3-butylene oxide:14.5 trans-2,3-butylene oxide.

Samples of the reaction mixture were taken at the time intervals indicated below. Results obtained by gas chromatography are also shown. Throughout the reaction time shown, temperature was maintained at about 25° C.

| Time | Analysis |
| --- | --- |
| 1½ hours | 8% conversion of butylene oxides |
| 3 hours | 78% conversion of butylene oxides (only 1,2-butylene oxide has reacted) |
| 5 hours | 82% conversion of butylene oxides (all 1,2-butylene oxide has reacted and cis-2,3-butylene oxide has begun to disappear |
| 6 hours | 90% conversion of butylene oxides |
| 20 hours | 92% conversion of butylene oxides (unreacted butylene oxides consist essentially of trans-2,3-butylene oxide). |

The reaction mixture remaining at the end of 20 hours was then heated to about 50° C. and maintained at that temperature for 8 hours. The reaction mixture was analyzed by gas chromatography and the product was found to contain 98 wt. %+ methyl ethyl ketone. The analysis shows only 0.6 wt. % of trans-2,3-butylene oxide remaining.

The foregoing demonstrates that 1,2-butylene oxide is isomerized much faster than cis-2,3-butylene oxide, which, in turn, is isomerized much faster than trans-2,3-butylene oxide.

The foregoing further demonstrates that an isomeric mixture of butylene oxides can be substantially completely isomerized according to the method of this invention to yield methyl ethyl ketone.

COMPARATIVE EXAMPLE

Using the same apparatus described in Example 1 600 mg. of dicobalt octacarbonyl was added to 6 ml. of isopropanol under an argon atmosphere and stirred for 1 hour. No gas evolution was observed. Then, 6 ml. of 1,2-butylene oxide was added via the addition funnel over a 15 minute period. Samples of the reaction mixture were collected at reaction times of 2 hours and 16 hours while maintaining reaction temperature at about 25° C. Results obtained by gas chromatography are shown below.

| Reaction Time | Analysis |
| --- | --- |
| 2 hours | 17% conversion of 1,2-butylene oxide to methyl ethyl ketone |
| 16 hours | 89% conversion of 1,2-butylene oxide to a product consisting of 3 wt. % butane, 90 wt. % methyl ethyl ketone and 7 wt. % hydroxy ethers. |

After stirring the reaction mixture at about 25° C. for 20 hours, the mixture was heated to 50° C. and maintained at that temperature for ½ hour. The reaction mixture was then analyzed by gas chromatography and the product was found to contain 2 wt. % butane, 94 wt. % methyl ethyl ketone, and 4 wt. % hydroxy ethers. A small amount of butyraldehyde (less than 0.3 wt. %) was also present.

Comparison of this Example with Example 1, supra, demonstrates the improved reaction rate and selectivities obtained when tertiary butyl alcohol solution of dicobalt octacarbonyl is employed as the isomerization media.

It is significant that a change in the color of the reaction mixture (from brown to purple-red) of this Comparative Example was observed after 2 hours reaction time. The color change was accompanied by a loss of methyl ethyl ketone selectivity for the system (see analytical results observed at 16 hours reaction time).

By contrast, no color change was observed over the reaction times of either Example 1 or Example 2.

What is claimed is:

1. An improved process for the preparation of methyl ethyl ketone by adding 1,2-butylene oxide to an alkanol solution of dicobalt octacarbonyl, thereby effecting a rearrangement of the epoxide to the ketone, the improvement comprising using tertiary butyl alcohol as the alkanol solent.

2. The method of claim 1 wherein an isomeric mixture of n-butylene oxides are added to the said catalyst solution.